United States Patent [19]

Ullman

[11] Patent Number: 4,624,929
[45] Date of Patent: Nov. 25, 1986

[54] SAMPLE COLLECTOR AND ASSAY DEVICE AND METHOD FOR ITS USE

[75] Inventor: Edwin F. Ullman, Atherton, Calif.

[73] Assignee: Syntex (U.S.A.) Inc., Palo Alto, Calif.

[21] Appl. No.: 677,144

[22] Filed: Dec. 3, 1984

[51] Int. Cl.$^4$ ............................ G01N 1/10; G01N 1/48
[52] U.S. Cl. ..................................... 436/179; 436/162;
436/165; 422/56; 422/59; 422/61; 422/70;
422/100; 73/864.54; 73/864.72; 73/864.91
[58] Field of Search ........................ 422/56, 58, 59, 61,
422/70, 100, 60; 73/864.17, 864.54, 864.72,
864.91; 436/162, 165, 174, 179

[56] References Cited

U.S. PATENT DOCUMENTS

| 2,967,093 | 1/1961 | Raymond | 436/179 |
|---|---|---|---|
| 3,675,490 | 7/1972 | Blomquist | 73/864.72 |
| 3,811,840 | 5/1974 | Bauer et al. | 422/56 |
| 3,846,077 | 11/1974 | Ohringer | 422/100 |
| 4,033,720 | 7/1977 | Silvestri | 436/162 |
| 4,133,211 | 1/1979 | Sarstedt | 73/864.17 |
| 4,151,832 | 5/1979 | Hamer | 422/58 |
| 4,268,270 | 5/1981 | Gabbay et al. | 422/58 |
| 4,366,241 | 12/1982 | Tom et al. | 422/56 |
| 4,409,182 | 10/1983 | Macklem | 422/58 |
| 4,435,504 | 3/1984 | Zuk et al. | 436/162 |

FOREIGN PATENT DOCUMENTS 171609 6/1960 Sweden ................................ 422/59

Primary Examiner—David L. Lacey
Attorney, Agent, or Firm—Theodore J. Leitereg

[57] ABSTRACT

A device is disclosed for collecting a liquid sample and diluting the liquid sample by virtue of being adapted for use with a container having a volume of diluting liquid. The device comprises a housing adapted for mating with the container where the mated housing and container form a chamber. A bibulous pad is attached to the housing for collecting a predetermined amount of a liquid sample. Additionally, the device, when used with the container, creates a pressure differential between the interior of the housing and the chamber. The pressure differential is sufficient to move a predetermined volume of the diluting liquid through the bibulous pad and into the housing. The device can be used for assaying for a component of a sample. The device has particular use in immunochromatography and for convenience can also contain a strip of bibulous material confined in the housing. In a method for collecting a liquid sample and subsequently diluting the sample with a predetermined volume of a liquid, the sample is collected on an bibulous pad at the base of a housing. The pad is designed to absorb a predetermined amount of the sample. Next, a pressure differential is created between the housing and a container having a volume of diluting liquid to cause a predetermined volume of the liquid to pass through the pad and into the housing.

38 Claims, 5 Drawing Figures

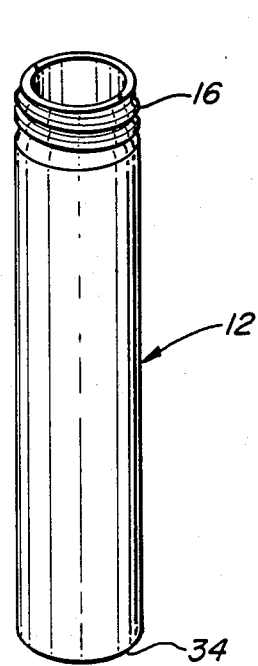
FIG._1.
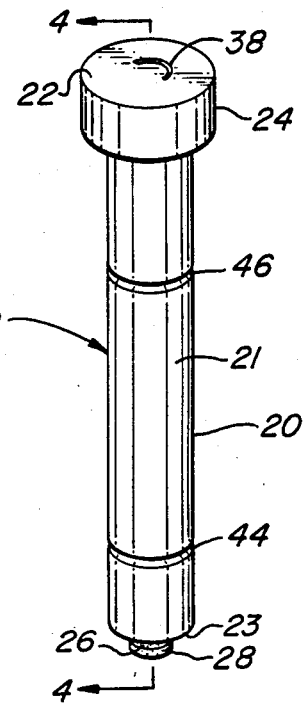
FIG._2.
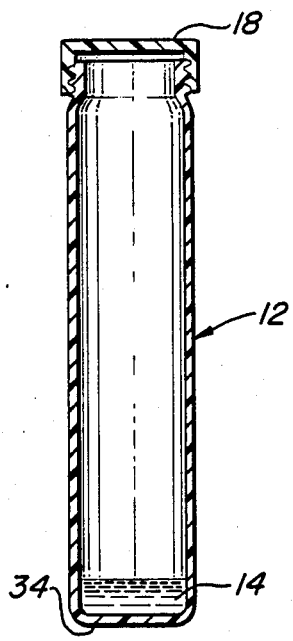
FIG._3.
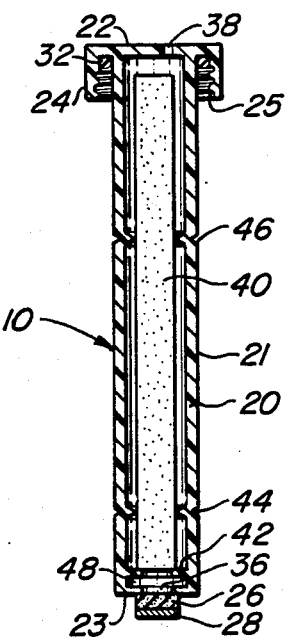
FIG._4.
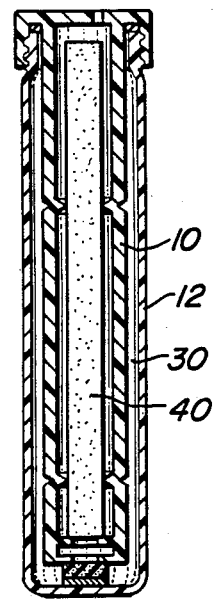
FIG._5.

SAMPLE COLLECTOR AND ASSAY DEVICE AND METHOD FOR ITS USE

BACKGROUND OF THE INVENTION

1. Field of the Invention

The invention relates to the dilution of a liquid sample with a second liquid in which the sample or component thereof is soluble. The quantitative mixing of a liquid sample with a solvent is required in a number of different areas including chromatography and assays.

The field of competitive protein binding assays or specific binding assays has greatly expanded, as its importance in the diagnostic field has become recognized. The ability to be able to detect a specific compound and measure the compound quantitatively has permitted the monitoring of the administration of a wide variety of drugs, the determination of an imbalance in a wide variety of hormones, the quantitation of physiologically active proteins, and the diagnosis of the presence of a pathogen.

In developing an assay, there are a number of considerations in devising the reagents and protocol. One consideration is the degree of sophistication of the individual performing the assay. There are many situations where it is desirable to have a relatively untrained individual carry out an assay and obtain reasonably quantitative results. It is particularly desirable that the relatively untrained individual be able to carry out a quantitative assay is a simple, rapid test without the need for sophisticated equipment. A critical element for carrying out a quantitative assay on a liquid sample is the collection and quantitative dilution of the liquid sample to be assayed.

2. Description of the Prior Art

An apparatus for precise mutual dilution and dosage of liquids is disclosed in U.S. Pat. No. 4,237,094. An adjustable diluting device is disclosed in U.S. Pat. No. 4,128,009. A plural piston, adjustable diluting device having a volume indicator assembly is described in U.S. Pat. No. 4,141,250.

SUMMARY OF THE INVENTION

The present invention is directed to a device for collecting a liquid sample wherein the device is adapted for use with a container having a volume of liquid for diluting the liquid sample. The device comprises a housing adapted for mating with the container, the mated housing and container forming a chamber. Means are attached to the housing for collecting a predetermined amount of a sample ("sample collecting means"). The device also includes means attached to the housing for mating with a container and thereby creating a pressure differential between the interior of the housing and the chamber when the device is mated with the container. The pressure differential is sufficient to move a predetermined volume of the liquid through the sample collecting means and into the housing. For chromatographic tests the device conveniently includes a strip of bibulous material confining in the housing. The device of the present invention finds particular use in immunochromatographic assays.

BRIEF DESCRIPTION OF THE DRAWINGS

FIG. 1 is a perspective view of a vial to which the device of the present invention is adapted for mating.

FIG. 2 is a perspective view of a device in accordance with the present invention.

FIG. 3 is a cross-sectional view of the vial of FIG. 1 with a cap.

FIG. 4 is a cross-sectional view of the device of FIG. 2 taken along lines 4—4.

FIG. 5 is a cross-sectional view of a device of FIG. 4 mated with the vial of FIG. 3.

DESCRIPTION OF THE SPECIFIC EMBODIMENTS

The present invention is a device for collecting a liquid sample, particularly for quantitatively collecting such a sample. The device is adapted for use with a container having a volume of liquid for quantitatively diluting the liquid sample. The device comprises a housing adapted for mating with a container where the mated housing and container form a chamber. Sample collecting means are attached to the housing for collecting a predetermined amount of a liquid sample. Means attached to the housing for mating with a container and during such mating creating a pressure differential between the interior of the housing and the chamber. The pressure differential is sufficient to move a predetermined volume of the liquid through the sample collecting means and into the housing.

An illustrative embodiment of the invention will now be described in detail, by way of example and not limitation, with reference to the attached drawings. Device 10 for diluting a liquid sample is depicted in FIGS. 2 and 4. The device is adapted for use with container 12, depicted in FIGS. 1 and 3, which contains a volume of liquid 14. Container 12 may be fabricated from any suitable material such as glass, plastic, and the like. Liquid 14 is generally a solvent in which the liquid sample to be diluted is soluble. Illustrative examples of such liquid medium for use in assays will be set forth hereinbelow. In general, the liquid medium can be water, organic or inorganic solvents, etc., and mixtures thereof. The top portion of vial 12 contains threads 16 by which cap 18 may provide a threaded closure of vial 12. The threaded portion of vial 12 is merely illustrative and other closure means may be employed, such as, for example, a friction fit, snap fit, and so forth.

Device 10 comprises housing 20 which is adapted at one end 22 for mating with vial 12. In the particular embodiment illustrated in the drawings, top portion 22 contains internal threading 24 compatible with the thread 16 on vial 12. Where other closure means are employed, the internal surface of top portion 22 will contain the appropriate means for mating with vial 12.

Means 26 for collecting a predetermined amount of a liquid sample ("sample collecting means") is attached to housing 20 at its other end. Sample collecting means 26 may take the form of a bibulous pad designed for absorbing a predetermined amount of the liquid sample. Such bibulous pads are known in the art, for example, one may use a pad such as that disclosed by Eastman Kodak (European Patent Application No. EP 13156, priority date of Dec. 27, 1978). Other examples of sample collecting means which can be employed in the present invention are porous pads comprised of paper, cellulosil sponge, polyvinylchloride, polyacrylamide, cellulose acetate, and the like.

The device can also include means 28 for removing excess liquid and filtering out particles from the liquid sample. Means 28 can be placed in overlying relationship with sample collecting means 26. Means 28 should be porous and removable. For example, one may use a pad of nylon mesh or mixtures of glass and synthetic fibers to filter out cells from a sample of whole blood. (See, for example, U.S. Pat. No. 4,477,575). Other suitable material for fabricating means 28 will be suggested to those skilled in the art in view of the disclosure contained herein.

Housing 20 depicted in FIGS. 2 and 4 has a continuous side wall 21, top wall 22 and bottom wall 23. Top wall 22 has a continuous side wall or sleeve portion 24 depending therefrom.

Device 10 further includes means attached to housing 20 for mating with vial 12 and during such mating creating a pressure differential in the interior of housing 20 and chamber 30 (FIG. 5). In the embodiment depicted in FIG. 5 housing 20 is placed inside vial 12 and top portion 22 of housing 20 is threaded onto vial 12 by means of thread 16. In the embodiment illustrated the pressure differential is created by air trapped in chamber 30 as housing 20 is threaded onto vial 12. The top portion of housing 20 includes means 32 for creating an airtight seal as housing 20 is threaded onto vial 12. Preferably, means 32 begins to form an airtight seal prior to the point at which housing 20 is fully threaded onto vial 12. Means 32 can be, for example, an O ring made of a resilient material, such as rubber. Any suitable elastomeric material can be used as long as it is not soluble in the liquid sample or the liquid medium.

The pressure differential created between the interior of housing 20 and chamber 30 should be sufficient to move a predetermined volume of liquid 14 through sample collecting means 26 and into housing 20. The pressure differential may be produced by any convenient means including a reduction in the gas volume occasioned by mating the housing and the vial, by pressure on the vial sufficient to deform the vial or by warming the vial. In the embodiment of the device of the invention depicted in the attached drawings, housing 20 is matingly sealed with vial 12 as a volume of air in chamber 30 is forced into the housing. The volume of air is sufficient to force a predetermined volume of liquid 14 through sample collecting means 26 and into housing 20.

The dimensions of housing 20 and container 12 should be such that upon the sealed mating of housing 20 and vial 12 sample collecting means 26 intimately contacts the inner bottom wall 34 of vial 12. Furthermore, the dimensions should be such that the volume of air trapped between the inner walls of vial 12 and the outer walls 21 of housing 20 be sufficient to force a predetermined volume of liquid 14 in vial 12 through sample collecting means 26 and into housing 20. In that regard, the bottom wall 23 of housing 20 should contain liquid entering means 36 which may be in the form of an opening or the like which allows the liquid from container 12 to enter housing 20.

In the situation where a volume of air is trapped in chamber 30 and forced into the interior of housing 20, housing 20 must also contain a means for venting the interior of the housing to the outside atmosphere. In the embodiment illustrated in the attached drawings, vent 38 is provided in top wall 22 of housing 20. The dimensions of vent 38, which can be in the form of a small opening that may be rectangular, circular, crescent-shaped, or the like, should be sufficient to allow the predetermined volume of liquid to efficiently pass into housing 20. The particular shape of vent 38 will be determined by the manner in which device 10 is used.

The device of the present invention finds particular use in diluting a liquid sample quantitatively for the purpose of conducting a chromatographic test, preferably for conducting an immunochromatography. For this purpose, device 10 can further include a strip of bibulous material 40 confined in housing 20. Strip 40 may conveniently be a strip of paper and generally has dimensions appropriate for the particular chromatographic test to be conducted. Housing 20 further includes means within housing 20 for maintaining strip 40 free from contact with liquid entering housing 20 until substantially all of the predetermined volume of liquid has contacted and passed through sample collecting means 26 and entered housing 20. Circumferential protrusion 42 in the interior bottom portion of housing 20 is designed to support strip 40 above the inner bottom wall 23 of housing 20. Basically, protrusion 42 forms a ledge upon which strip 40 rests. Strip 40 is prevented from touching side wall 21 of housing 20 by circumferential protrusions 44 and 46 in the inner side of wall 21 of housing 20. Protrusions 42, 44 and 46 have dimensions such that strip 40 is maintained essentially parallel with respect to wall 21 of housing 20.

As mentioned above, protrusion 42 supports strip 40 and elevates it from bottom wall 23 of housing 20. As a result, void 48 is created in the bottom portion of housing 20. Generally, the volume of void 48 should be less than the predetermined volume of liquid entering the bottom portion of housing 20 so that when the predetermined volume of liquid has entered housing 20, the bottom portion of strip 40 is in contact with the liquid. Where a paper strip 40 is employed, vent 38 is conveniently crescent-shaped in order to allow entry of the paper strip in device 10 during manufacture and prevent the paper strip from exiting housing 20 through vent 38. In this respect, vent 38 will have dimensions sufficient to accommodate paper strip 40.

Device 10 can be constructed in any convenient manner. For example, housing 20 may be molded in one piece. Alternately, housing 20 may be assembled from pieces which may include two longitudinal halves which may be bought together and sealed in an appropriate manner, such as, for example, sonic welding, adhesives, solvent adhesion, or the like. Furthermore, it is possible to assemble housing 20 and then add top portion 22 by appropriate sealing means such as those described above.

The use of the device of the present invention as applied to immunochromatography will next be described in detail. In the subsequent description, the following definitions will be used.

Analyte—The compound or composition to be measured, which may be a ligand, which is mono- or polyepitopic, antigenic or haptenic, a single or plurality of compounds which share at least one common epitopic site or a receptor.

Specific Binding Pair Member ("sbp" member)—Two different molecules, where one of the molecules has an area on the surface or in a cavity which specifically binds to a particular spatial and polar organization of the other molecule. The members of the specific binding pair are referred to as ligand and receptor ("anti-ligand"). For the most part, the receptor will be an antibody and the ligand will serve as an antigen or hapten and to that extent are members of an immunological pair.

Ligand—Any organic compound for which a receptor naturally exists or can be prepared.

Receptor ("Anti-Ligand")—Any compound or composition capable of recognizing a particular spatial and polar organization of a molecule, i.e., epitopic site.

Illustrative receptors include naturally occurring receptors, e.g. thyroxin binding globulin, antibodies, enzymes, FAB fragments, lectins and the like.

Label—The label may be any molecule conjugated to another molecule or support and, where two molecules are involved, is arbitrarily chosen as to which molecule is the label. In the subject invention, the labels will be an sbp member which is conjugated to a support or a member of the signal producing system that is conjugated to a support or an sbp member.

Signal Producing System—The signal producing system may have one or more components, at least one component being conjugated to an sbp member. The signal producing system produces a measurable signal which is detectable by external means, normally by measurement of the electromagnetic radiation, desirably by visual examination. For the most part, the signal producing system involves chromophores and enzymes, where chromophores include dyes which absorb light in the ultraviolet or visible region, phosphors, fluorescers and chemiluminescers.

Immunochromatograph—The immunochromatograph has a plurality of sbp members, either ligand or receptor, bound in an region to a bibulous support which allows for the movement of a liquid across the region with transport of the analyte and, as appropriate, any members of the signal producing system. The sbp members are non-diffusively bound to the support, either covalently or non-covalently. In addition, one or more members of the signal producing system may be non-diffusively bound to the bibulous support, either covalently or non-covalently.

As mentioned above, the device of the present invention can be employed to determine the result of a chemical test particularly where a chromatographic step is employed. The present device finds particular application in a method for determining quantitatively the amount of an analyte in a sample suspected of containing the analyte. In this preferred use, strip 40 is an immunochromatograph. Examples of immunochromatographs and method of using the same are described in U.S. Pat. Nos. 4,168,146 and 4,435,504, the disclosures of which are incorporated herein by reference.

The known immunochromatographic method is carried out on a bibulous strip, e.g., strip 40, involving a stationary solid phase and a moving liquid phase. The stationary solid phase can be contacted with a plurality of reagents in a number of different solutions.

The region in which the sbp member is non-diffusively bound to the bibulous strip is referred to as the "immunosorbing zone". The analyte from the sample will traverse this zone being carried along with a solvent whose front crosses the zone. The analyte, which is the homologous or reciprocal sbp member to the sbp member bound to the support, becomes bound to the support through the intermediacy of sbp member complex formation. The signal producing system provides the manner by which the area in the immunosorbing zone to which the analyte is bound may be distinguished from the area in which it is absent, so that the distance from a predetermined point on the immunochromatograph is a measure of the amount of analyte in the sample.

The incremental movement of the sample through the immunosorbing zone results from dissolving a liquid sample in an appropriate liquid medium or solvent (14) and the transport of the resulting solution through the immunosorbing zone due to capillarity.

For immunochromatography the solvent will normally be an aqueous medium, which may be up to about 40 weight percent of other polar solvents, particularly oxygenated solvents of from 1 to 6, more usually of from 1 to 4 carbon atoms, including alcohols, ethers and the like. Usually, the cosolvents will be present in less than about 20 weight percent.

The pH for the medium will usually be in the range of 4-11, more usually 5-10, and preferably in the range of about 6.5-9.5. The pH is chosen to maintain a significant level of binding affinity of the sbp members. Various buffers may be used to achieve the desired pH and maintain the pH during the elution. Illustrative buffers include borate, phosphate, carbonate, tris, barbital and the like. The particular buffer employed is not critical, but in individual assays, one buffer may be preferred over another.

Desirably, from about 0.05 to 0.5 wt. % of a non-ionic detergent is included with the sample. Various polyoxyalkylene compounds may be employed of from about 200 to 20,000 daltons.

Moderate, and desirably substantially constant, temperatures are normally employed for carrying out the assay. The temperatures for the chromotography and production of a detectable signal will generally be in the range of about 10°-50° C., more usually in the range of about 15°-50° C., and frequently will be ambient temperatures, that is, about 15°-25° C.

The concentration, in the liquid sample, of analyte which may be assayed will generally vary from about $10^{-4}$ to about $10^{-15}$M, more usually from about $10^{-6}$ to $10^{-14}$M. Considerations, such as the concentration of the analyte of interest and the protocol will normally determine the concentration of the other reagents.

When the concentrations of many of the various reagents in the sample and reagent solutions will generally be determined by the concentration range of interest of the analyte, the final concentration of each of the reagents will normally be determined empirically to optimize the sensitivity of the assay over the range of interest. However, with certain protocols, individual reagents may be used in substantial excess without detrimentally affecting the sensitivity of the assay.

The size of the immunosorbing zone need have no upper limit, except for practical considerations as mentioned earlier. Since, for the most part, low concentrations are being assayed, the width of the immunoabsorbing zone will tend to be relatively narrow, so that the analyte can traverse a reasonable distance and provide for reasonable differentiation over the concentration range of interest. Generally, the width of the strip 40 will not be less than about 0.2 mm and not more than about 2 cm, generally ranging from about 5 mm to 20 mm, preferably from about 5 mm to 15 mm.

The length of the immunoabsorbing zone will be desirably at least about 2 to 10 times the width, usually at least about 2 mm, more usually at least about 10 mm, preferably at least about 23 mm, and not more than about 12 cm, usually not more than about 10 cm, preferably from about 5 to 10 cm. The distance traversed is a factor in the time required for the assay, which will be taken into account with the other factors affecting the time required for the assay.

Other reagents which are members of the signal producing system may vary widely in concentration depending upon the particular protocol and their role in signal production. In a "true" competitive situation between a labeled sbp member and the analyte, usually the labeled sbp member will not exceed 10 times the maximum concentration of interest of the analyte and will not be less than about 0.5 times the minimum concentration of interest. In most other situations, the amount of the other reagents involved in sbp member complex formation may be present in an amount substantially less than the binding equivalent of analyte or in substantial excess to the binding equivalent of analyte. Therefore, no simple relationship can be provided.

In carrying out the assay, the protocol will normally involve dissolving the sample into the eluting solvent. The sample may be derived from a wide variety of sources, such as physiologic fluids, illustrated by saliva, blood, serum, plasma, urine, ocular lens fluid, spinal fluid, etc., chemical processing streams, food, pesticides, pollutants, etc.

The bottom end of device 10 (i.e., the end of device 10 that contains sample collecting means 26 and filtering means 28) will then be contacted with the liquid sample. The liquid sample is absorbed by means 26 in a predetermined amount. Means 28 acts to remove excess liquid sample and to filter out particles such as cellular debris and the like from the liquid sample. Means 28 is then removed from device 10. Device 10 is then threaded onto vial 12 containing liquid medium 14, in this case, a buffered aqueous medium as described above which may contain one or more members of the signal producing system. Where a member of the signal producing system is present, at least one member will be conjugated to an sbp member to provide an sbp member-label conjugate.

As device 10 is threaded into vial 12, a seal is formed and a volume of air is trapped in chamber 30. Positive pressure, exerted on liquid medium 14, forces a predetermined volume of the liquid medium through means 26, which now intimately contacts the inner bottom wall 34 of vial 12. As medium 14 passes through means 26, it dilutes the predetermined volume of liquid sample. The force of this passage should be sufficient to provide rapid and complete dilution of the liquid sample as the diluted mixture passes into the interior of housing 20 through opening 36 into void 48. In void 48 the liquid medium contacts an end portion of strip 40. Liquid medium 14 then begins its traversal of strip 40 by capillary action.

Sufficient time will be allowed for the liquid front to complete traversal of the immunosorbing zone which can be determined by viewing the strip. The zone has sufficient sbp member to insure that all of the analyte becomes bound in said zone without exhausting the sbp member bound in the zone.

Where the immunochromatograph is not standardized to the extent that variations in conditions may change the distance the analyte traverses, a standard sample can be provided having a known amount of analyte. The analyte sample and the standard can be run at the same time, and a quantitative comparison can be made between the standard sample and the analyte sample. If necessary, more than one standard can be employed, so that the distance traversed can be graphed for the different concentrations and used to quantitate a particular sample.

For the most part, relatively short times are involved for the immunochromatograph. Usually, the traverse of the liquid through the immunosorbing zone will take at least 30 sec and not more than 1 hour, more usually from about 1 min to 30 min. The development of the signal will generally range from 30 sec to 30 min, more usually from about 30 sec. to 5 min.

The signal producing system has at least one enzyme and may have two or more other components of the signal producing system or one or more substrates, and may also include coenzymes. Any member of the signal producing system may be employed as a label, where the presence of the label on the immunochromatograph provides for a substantial change in signal in the area of the label. Therefore, labels may include enzymes or coenzymes. Usually, the label will be an enzyme.

The individual or combination of enzyme labels may be varied widely. The product producing the detectable signal may be a dye, fluorescer or chemiluminescer, with the signal detected by visual observation, due to absorption, fluorescence, or chemiluminescence, or a spectrophotometric measurement, employing measuring absorption, reflectance, fluoroescence or chemiliminescence.

For the most part the enzymes of interest will be oxidoreductases and hydrolases. A large number of enzymes of interest are set forth in U.S. Pat. No. 4,275,149 the relevant portion of which is incorporated herein by reference. For combinations of enzymes one enzyme is non-diffusively bound to the immunochromatograph, while the other enzyme is conjugated to a sbp member.

After the liquid has traversed the immunosorbing zone, if the label-sbp member conjugate was not combined with the sample, the immunosorbing zone is contacted substantially uniformly with a solution having labeled-sbp member conjugate and depending on the label and protocol one or more other members of the signal producing system. This may be accomplished by removing device 10 from vial 12 and introducing device 10 into a container having the appropriate solution. The container can be vial 12 itself or some other suitable container. Alternately, the solution may be added to the interior of housing 20 through vent 38 without removal of device 10 from vial 12.

In the case of an enzyme-sbp member conjugate the immunosorbing zone is contacted with a solution of enzyme-sbp member conjugate and substrate, optionally with a scavenger. In this situation an enzyme is bound to the immunochromatograph in the immunosorbing zone,, which is related to the enzyme bound to the sbp member, by the substrate of one being the product of the other. The enzyme-sbp member conjugate will normally be in an aqueous buffered solution and may be present in substantial excess of available binding sites. The pH range and buffers have been previously considered. After a sufficient time for the enzyme-sbp member conjugate to bind either to ligand or receptor, and for color to form, the immunochromatograph is removed from the solution.

By having the two enzymes, a step in the protocol is eliminated since the enzyme-sbp member conjugate and substrate may be combined in the same solution without reaction prior to contacting the immunosorbing zone.

After the enzyme-sbp member conjugate is bound to the immunochromatograph by being present in the sample, the immunochromatograph is developed by immersion in a substrate solution. In this case an enzyme may or may not be bound to the immunochromatograph. The addition of substrate or developer solution to device 10 can be accomplished in the same manner as described above.

With a coenzyme label, the developer solution will usually contain one or more enzymes to provide for regeneration of the coenzyme and substrate. Since the enzymatic reaction requires the coenzyme, the enzyme and substrate can be combined as a single developer reagent without any reaction prior to contact with the immunosorbing zone.

The substrates will vary with the enzymes and are normally in substantial excess, so as not to be rate limiting (greater concentration than Km). The aqueous solution will usually be appropriately buffered for the enzyme system and may include a scavenger for the product of the enzyme which is the substrate of the other enzyme, e.g., catalase for hydrogen peroxide from uricase.

Strip 40 in device 10 is contacted with the developer solution for a sufficient time to produce a detectable signal producing compound so as to define the region of the immunosorbing zone in which the analyte is bound. Once the detectable signal has been produced, the distance from one end of the chromatograph may be measured as a quantitative measure of the amount of analyte in the sample.

While some distortion may be observed at the border, in most situations the border is reasonably well defined, so that changes in concentration of factors of two or less in the $\mu$g to pg range can be detected with a wide variety of analytes. Thus, by employing an appropriate cye precursor as a substrate, the amount of an analyte can be quantitatively determined by visual observation with a single measurement (the sample) by the user and a two-step protocol which is relatively insensitive to interference.

The ligand analytes are characterized by being monoepitopic or polyepitopic, while the receptor analytes may have a single or plurality of binding sites. The polyepitopic analytes will normally be poly(amino acids), i.e., polypeptides and proteins, polysaccharides, nucleic acids, and combinations thereof. Such combinations or assemblages include bacteria, viruses, chromosomes, genes, mitochondria, nuclei, cell membranes and the like.

For the most post, the polyepitopic ligand analytes will have a molecular weight of at least about 5,000, or usually at least about 10,000. In the poly(amino acid) category, the poly(amino acids) of interest will generally be from about 5,000 to 5,000,000 molecular weight, more usually from about 20,000 to 1,000,000 molecular weight, and among hormones of interest, about 5,000 to 60,000 molecular weight.

An extensive listing of useful ligands may be found in U.S. Pat. No. 4,275,149, the disclosure bridging columns 12 to 17, which disclosure is incorporated herein by reference.

The monoepitopic ligand analytes will generally be from about 100 to 2,000 molecular weight, more usually from about 125 to 1,000 molecular weight. The analytes of interest include drugs, metabolites, pesticides, pollutants, and the like.

A large number of analytes of interest are listed in U.S. Pat. No. 4,275,149, columns 17 and 18, which disclosure is incorporated herein by reference.

For receptor analytes, the molecular weights will generally range from about $10^4$ to $2\times10^8$, more usually from about $3\times10^4$ to $2\times10^6$. For immunoglobulins, e.g., IgA, IgD, IgE, IgG and IgM, the molecular weights will generally vary from about 160,000 to about $10^6$. Enzymes will normally vary from about 10,000 to 600,000 daltons. Natural receptors vary widely, being generally at least about 25,000 molecular weight and may be $10^6$ and higher, including such materials as avidin, thyroxine binding globulin, thyroxine binding prealbumin, transcortin, membrane surface proteins, etc.

Where a ligand is conjugated to another molecule or support, frequently the ligand will be modified to provide for a particular functional group at a particular site. This modification produces a product referred to as a ligand analog. U.S. Pat. No. 4,275,149 also has an extensive description of ligand analogs, bridging columns 18 and 19, which description is incorporated herein by reference.

The immunochromatograph involves a bibulous support providing liquid travel through capillarity, a non-diffusively bound sbp member, and may also include one or more members of the signal producing system.

A wide variety of bibulous materials may be used for the strip 40 which include both natural and synthetic polymeric materials, particular cellulosic materials, such as fiber containing papers, e.g., filter paper, chromatographic paper, etc., synthetic or modified natural occurring polymers, such as poly(vinyl chloride), crosslinked dextran, acrylates, etc. either used by themselves or in conjunction with a ceramic material, such as silica.

The thickness of the immunochromatograph bibulous support will generally vary from about 0.05 mm to about 2 mm, more usually being about 0.1 mm to 0.5 mm, preferably from about 0.2 mm to about 0.4 mm. The structure can be varied widely and includes fine, medium fine, medium, medium coarse and coarse. The surface can be varied widely with varying combinations of smoothness and roughness combined with hardness and softness.

The immunochromatograph can be supported by a variety of inert supports, such as Mylar, polystyrene, polyethylene, or the like. The supports can be used as a backing spaced from the immunochromatograph, edging, or other structure to enhance the mechanical integrity of the immunochromatograph. The immunochromatograph can be coated with a wide variety of materials to provide for enhanced propeties. Coatings may include protein coatings, polysaccharide coatings, sugars or the like, which are used particularly to enhance the stability of the materials conjugated to the support. These compounds can also be used for improved binding of the materials, such as the sbp member or signal producing system member bound to the immunochromatograph.

The immunochromatograph can be activated with reactive functionalities to provide for covalent bonding of the organic materials to be conjugated to the support-such as those described in U.S. Pat. No. 4,168,146.

The amount of sbp member which is bound to the support will vary depending upon the size of the support and the amount required to bind all of the analyte and, as required, labeled sbp member. Generally, the amount of sbp member will range from about $10^{-5}$ to $10^{-14}$ moles/cm$^2$, more usually from about $10^{-7}$ to $10^{-12}$ moles/cm$^2$. The number of moles per unit area will be varied in order to insure that there is sufficient discrimination in the concentration range of interest for the distance traversed by the analyte.

In a preferred embodiment, a signal producing system member is non-diffusively bound to the bibulous support. Particularly, an enzyme is bound to the support which will interact with the labeled sbp member, where the label is another enzyme. In relationship of the enzymes will be discussed in the description of the signal producing system.

Both the sbp member and the signal producing system member may be bound to a variety of supports by adsorption, rather than covalent bonding. This will involve contacting the bibulous support with the solution containing the sbp member and/or signal producing member, removing the immunochromatograph from the solution, and allowing the immunochromatograph to dry. Alternatively, the solution may be applied by spraying, painting, or other technique which will provide uniformity.

Generally, relatively large sheets will be used which can then be cut to the appropriate dimensions. The edges of strip 40 can be modified to control the shape of the front of the traversing component. Such modification includes serration and chemical treatment of the edges as described in U.S. Ser. No. 591,155, filed Mar. 16, 1984, the disclosure of which is incorporated herein by reference. The edges of strip 40 can also be cut by non-compressive means such as by laser means as disclosed in U.S. Ser. No. 599,386, filed Apr. 12, 1984, the disclosure of which is incorporated herein by reference.

The signal producing system will, for the most part, involve the production of a detectable signal involving the absorption or emission of electromagnetic radiation, particularly light in the ultraviolet and visible region, more particularly radiation having a wavelength in the range of about 400 to 800 nm. Because of the nature of the immunochromatograph, in order to have a detectable signal, it is necessary that there be a sufficient concentration of the label over a unit area. Therefore, for the most part, individual labels will not be sufficient to provide the desired sensitivity. To that extent, means must be provided for the generation of a plurality of detectable molecules associated with a single labeled sbp member, where the label which provides the means for such generation does not interfere with the traversing of the labeled sbp member, when the labeled sbp member traverses the immunosorbing zone. Therefore, one employs a label which produces a large number of molecules which can be detected, such as an enzyme or coenzyme. Amplification is then obtained by the presence of a single label.

An enzyme or coenzyme is employed which provides the desired amplification by producing a product, which absorbs light, e.g., a dye, or emits light upon irradiation or chemical reaction, a fluorescer, or chemiluminescer. A larger number of enzymes and coenzymes for providing such products are indicated in U.S. Pat. No. 4,275,149 bridging columns 19 to 23, and U.S. Pat. No. 4,318,980, columns 10 to 14, which disclosures are incorporated herein by reference.

Of particular interest is the use of a combination of enzymes, where the enzymes are related by the product of one enzyme being the substrate of the other enzyme. In this manner, non-specific interference is substantially reduced and the border between the zones containing the bound analyte and free of analyte is more effectively defined.

A number of enzyme combinations are set forth in U.S. Pat. No. 4,275,149, bridging columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, e.g., peroxidase, microperoxidase, and cytochrome C oxidase. Additional enzyme combinations may be found in the subject matter incorporated by reference. While the above oxidoreductase combination is preferred, other enzymes may also find use such as hydrolases, transferases, and oxidoreductases other than the ones indicated above.

Illustrative coenzymes which find use include NAD[H]; NADP[H], pyndixal phosphate; FAD[H]; FMN[H], etc., usually coenzymes involving cycling reactions, see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

By appropriate manipulation or choice of the label-sbp member conjugate, the receptors, the bibulous support and the conditions employed in performing the assay, two different embodiments of the subject invention can be achieved where the analyte and enzyme-sbp member are applied to the immunochromatograph in the same solution. In one embodiment, the region of the immunosorbing zone traversed by the analyte is observable due to production of the detectable signal substantially uniformly throughout the region in which the analyte is present. In the other embodiment, the detectable signal is primarily observable at a border related to the region in the immunosorbing zone occupied by the analyte.

The different results may be related to different binding constants, rates of travel, adsorption or the like, of the label-sbp member conjugate as compared to the analyte. The variations can be achieved by varying the number of sbp members, particularly haptenic analytes, bound to the labels, varying the binding specificity of receptors bound to the bibulous support, e.g., by preparing antibodies to an immunogen having one linking group between the hapten analyte and antigen and employing a different linking group with the label-hapten analyte conjugate, varying the solvent and/or support to vary the Rf factors, or other techniques.

As a result of the use of two enzymes in the signal producing system with one enzyme as a label, a simplified protocol can be employed, also a strong detectable signal is obtained providing for accurate delineation of the front to which the analyte progressed. By having the product of the enzyme bound to the bibulous support be the substrate of the enzyme conjugated to the sbp member, a sharp, rapid and uniform development of the detectable signal is observed on the immunochromatograph. Furthermore, one establishes a high localized concentration of substrate for the enzyme bound to the immunochromatograph, so as to encourage the rapid deposit of the detectable signal producing compound at the surface.

As a matter of convenience, the present device can be provided in a kit in packaged combination with predetermined amounts of reagents for use in assaying for an analyte. Where two enzymes are involved, the reagents will include enzyme labeled sbp member, substrate for the enzyme bound to the immunochromatograph, any additional substrates and cofactors required by the enzymes, and the dye precursor, which provides the detectable chromophore or fluorophore. In addition, other additives may be included, such as stabilizers, buffers, and the like. The relative amounts of the various reagents may be varied widely, to provide for concentrations in solution of the reagents which substantially optimize the sensitivity of the assay. The reagents can be provided as dry powders, usually lyophilized, including excipients, which on dissolution will provide for a reagent solution having the appropriate concentrations for performing the assay. For convenience, where the reagents are in the liquid state, some or all of the reagents can be provided in a container, e.g., vial 12.

Although the foregoing invention has been described in some detail by way of illustration and example for the purposes of clarity and understanding, it will be obvious that certain changes or modifications may be practiced within the scope of the appended claims.

What is claimed is:

1. A device for collecting a liquid sample, which device comprises:

a housing, means attached to said housing for collecting a predetermined amount of a liquid sample, said means comprising a bibulous pad designed to absorb and hold said predetermined amount of liquid sample, and means attached to said housing for mating said device with a container having a volume of liquid for dilution of said liquid sample and during said mating creating a pressure differential between the interior of said housing and a chamber formed by said mated housing and container, said pressure differential being sufficient to move a predetermined volume of the liquid through said means attached to said housing for collecting a predetermined amount of a liquid sample and into said housing.

2. The device of claim 1 in which further includes a strip of bibulous material confined in said housing.

3. The device of claim 2 wherein said strip of bibulous material is a paper strip.

4. The device of claim 2 which further includes means within said housing for maintaining said strip of bubulous material free from contact with said housing.

5. The device of claim 2 wherein said strip of bibulous material contains reagents for performing a chromatographic test.

6. The device of claim 2 wherein said strip of bibulous material contains reagents for performing an immunochromatography.

7. A kit comprising in combination:
    (a) the device of claim 2,
    (b) a container capable of mating with the device of claim 2, and
    (c) reagents for conducting a chromatographic test.

8. The kit of claim 7 wherein the reagents are immunochromatographic test conducting reagents.

9. The device of claim 1 which further includes means for removing excess liquid and filtering out particles from said sample, said means being removable, porous and in overlying relationship to said sample collecting means.

10. The device of claim 1 wherein said housing comprises a continuous side wall and top and bottom walls.

11. The device of claim 1 wherein said means for mating includes an air-tight seal.

12. The device of claim 11 wherein said seal is an O-ring.

13. The device of claim 1 wherein said housing includes means for venting the interior of said housing to the outside atmosphere.

14. The device of claim 1 which further includes an opening in the bottom of said housing.

15. The device of claim 1 wherein said means for mating includes means for concomitantly sealing said housing in the container and forcing a volume of air in said chamber into said housing, said volume of air being sufficient to force the 16. In combination, a container having a predetermined volume of liquid for diluting a liquid sample and a device for collecting a liquid sample, which device comprises:

a housing, means attached to said housing for sealed mating of said device with said container, means incorporated with said housing for providing an air-tight seal during the mating of said housing and said container, means attached to said housing for collecting a predetermined amount of a sample, said means comprising a bibulous pad designed to absorb and hold said predetermined amount of liquid sample, means for venting the interior of said housing to the outside atmosphere, and means incorporated into said housing for allowing the liquid to enter said housing, the dimensions of said housing in conjunction with the dimensions of said container being such that upon sealed mating of said housing and said container a volume of air between the inner walls of said container and the outer walls of said housing forces substantially all of the predetermined volume of the liquid through said means attached to said housing for collecting a predetermined amount of a sample and into said housing through said means incorporated into said housing for allowing the liquid to enter said housing.

17. The device of claim 16 which further includes a strip of bibulous material confined in said housing.

18. The device of claim 17 which further includes means within said housing for maintaining the strip of bibulous material free from contact with said housing.

19. The device of claim 16 which further includes means for removing excess liquid and filtering out cells and cellular debris, said means being removable, porous, and in overlying relationship to said sample collecting means.

20. In combination a device for collecting a liquid sample and a vial containing a volume of a liquid medium comprising reagents for a chromatographic test, said vial having threaded closure means, said device comprising:

a housing formed by a continuous side wall and top and bottom walls, a bibulous pad attached to the outside of the bottom wall of said housing, said bibulous pad being designed to absorb and hold a predetermined amount of a liquid sample, an opening to the outside atmosphere in the top wall of said housing, and an opening in the bottom wall of said housing permitting fluid communication through said bibulous pad to the interior of said housing, said top wall having threaded means compatible with the threaded closure means of said vial, said threaded means including means for forming an air-tight seal between said housing and said vial, the dimensions of said housing and said vial being such that upon the sealed closure of said housing into said vial said bibulous pad intimately contacts the bottom of said vial and a volume of air is trapped between said housing and said container sufficient to force a predetermined volume of liquid medium in said vial for diluting said liquid sample through said bibulous pad and concomitantly into said housing.

21. The device of claim 20 which further includes a paper strip confined in said housing.

22. The device of claim 21 which further includes a circumferential protrusion in an interior bottom portion of said housing, said protrusion creating a void in the bottom portion of said housing.

23. The device of claim 20 which further includes a removable, porous pad in overlying relationship to said bibulous pad.

24. A device for diluting a liquid sample, which comprises:
a first chamber formed by side and top and bottom walls,
a bibulous pad attached to the outside of the bottom wall of said first chamber, said bibulous pad being designed to absorb and hold a predetermined amount of a liquid sample,
an opening to the outside atmosphere in the top wall of said first chamber, and
an opening in the bottom wall of said first chamber permitting fluid communication through said pad to the interior of said first chamber,
a second chamber containing a volume of a liquid, said second chamber formed by side and bottom walls,
means incorporated in said top wall of said first chamber for sealing said second chamber so as to force a volume of air into said first chamber, said volume of air being sufficient to move a predetermined volume of liquid through said pad and into said first chamber thereby diluting said sample.

25. The device of claim 24 which further comprises a paper strip confined in said first chamber.

26. The device of claim 25 which further includes a circumferential protrusion in an interior bottom portion of said first chamber to maintain said strip free from contact with the inner bottom wall of said first chamber.

27. The device of claim 24 which further includes a removable porous pad in overlying relationship to said bibulous pad.

28. A method for diluting a liquid sample with a predetermined volume of a liquid, which comprises:

(a) collecting said sample on a bibulous pad at the base of a housing, said pad being designed to absorb and hold a predetermined amount of said sample, and (b) creating a pressure differential between said housing and a container having a volume of liquid for dilution of said liquid sample to cause a predetermined volume of said liquid to pass through said pad and move into the housing, said sample or a component thereof being soluble in said liquid.

29. The method of claim 28 wherein said pressure differential is created by concomitantly sealing the container and trapping a volume of air sufficient to force said predetermined volume of liquid through said pad.

30. The method of claim 28 wherein the housing contains a strip of bibulous material and the predetermined volume of liquid, with the sample or a component thereof dissolved therein, contacts a portion of the strip.

31. The method of claim 30 wherein the strip of bibulous material is maintained free from contact with the inner bottom wall of said housing.

32. The method of claim 30 wherein said strip of bibulous material is a paper strip.

33. The method of claim 30 wherein said strip of bibulous material contains reagents for performing a chromatographic test.

34. The method of claim 30 wherein said strip of bibulous material contains reagents for performing an immunochromatography.

35. The method of claim 28 wherein said liquid sample contains particles and said particles are removed therefrom prior to creating the pressure differential.

36. The method of claim 28 wherein the housing contains a continuous side wall and top and bottom walls.

37. The method of claim 28 wherein an air-tight seal is employed to create said pressure differential.

38. In a kit containing reagents for conducting an immunochromatography, the improvement which comprises included with said kit a device for collecting a liquid sample, which device comprises:
a housing
a strip of bibulous material confined in said housing,
means attached to said housing for collecting a predetermined amount of a liquid sample, said means comprising a bibulous pad designed to absorb and hold said predetermined amount of liquid sample, and
means attached to said housing for mating said device with a container having a volume of liquid for dilution of the liquid sample and during said mating creating a pressure differential between the interior of said housing and a chamber formed by said mated housing and container, said pressure differential being sufficient to move a predetermined volume of the liquid through said means attached to said housing for collecting a predetermined amount of a liquid sample and into said housing.

* * * * *